United States Patent [19]

Grinfeld et al.

[11] Patent Number: 5,312,344
[45] Date of Patent: May 17, 1994

[54] ARTERIAL PERFUSION CANNULA FOR EXTRACORPOREAL CIRCULATION AND OTHER USES

[76] Inventors: Roberto R. Grinfeld; Liliana R. Grinfeld, both of Gascon 626, Capital, Argentina

[21] Appl. No.: 103,557

[22] Filed: Aug. 9, 1993

Related U.S. Application Data

[63] Continuation of Ser. No. 737,358, Jul. 29, 1991.

[30] Foreign Application Priority Data

Feb. 25, 1991 [AR] Argentina .............................. 319116

[51] Int. Cl.⁵ .............................................. A61M 25/00
[52] U.S. Cl. ................................. 604/101; 606/194; 604/96; 128/656
[58] Field of Search .................... 604/96–101, 604/264, 280; 128/656; 606/191, 192, 194

[56] References Cited

U.S. PATENT DOCUMENTS

| | | | |
|---|---|---|---|
| 4,610,662 | 9/1986 | Weikl | 604/101 |
| 4,636,195 | 1/1987 | Wolinsky | 604/101 |
| 4,676,778 | 6/1987 | Nelson, Jr. | 604/101 |
| 4,877,031 | 10/1989 | Conway et al. | 604/96 |
| 5,046,503 | 9/1991 | Schweiderman | 604/96 |
| 5,059,177 | 10/1991 | Towne et al. | 604/96 |
| 5,090,960 | 2/1992 | Michael | 604/96 |
| 5,135,474 | 4/1992 | Swan et al. | 604/101 |
| 5,135,484 | 8/1992 | Wright | 604/101 |
| 5,147,377 | 9/1992 | Sahota | 604/96 |

*Primary Examiner*—C. Fred Rosenbaum
*Assistant Examiner*—Chalin Smith
*Attorney, Agent, or Firm*—Bachman & LaPointe

[57] ABSTRACT

Arterial perfusion cannula, for extracorporeal circulation and related uses. The distal end may be inserted into the ascending aorta, or into the femoral artery and the other part is to be connected to a cardio-pulmonary machine, comprising a multi-channel catheter formed by at least three pathways two of which correspond to the inlet of blood flow, provided with openings which, being interconnectable to the aortic vessel, are located in two different points of the cannula's distal end, the third pathway channelizing a fluid feeding at least one inflatable balloon, located between said interconnecting openings, as an arterial occlusive element adjustable against the inner vessel walls.

5 Claims, 2 Drawing Sheets

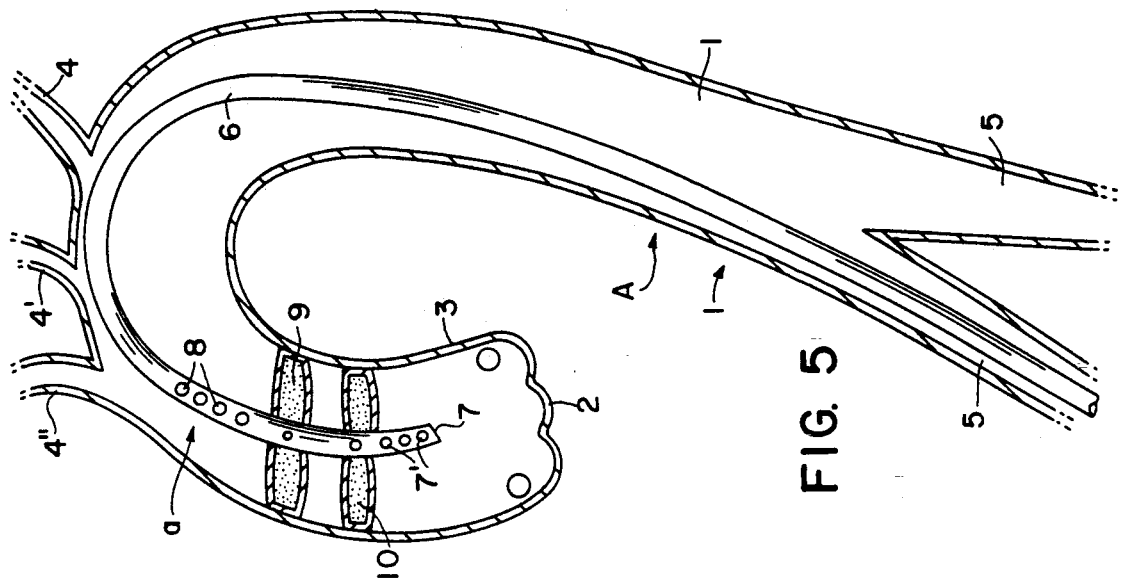
FIG. 5
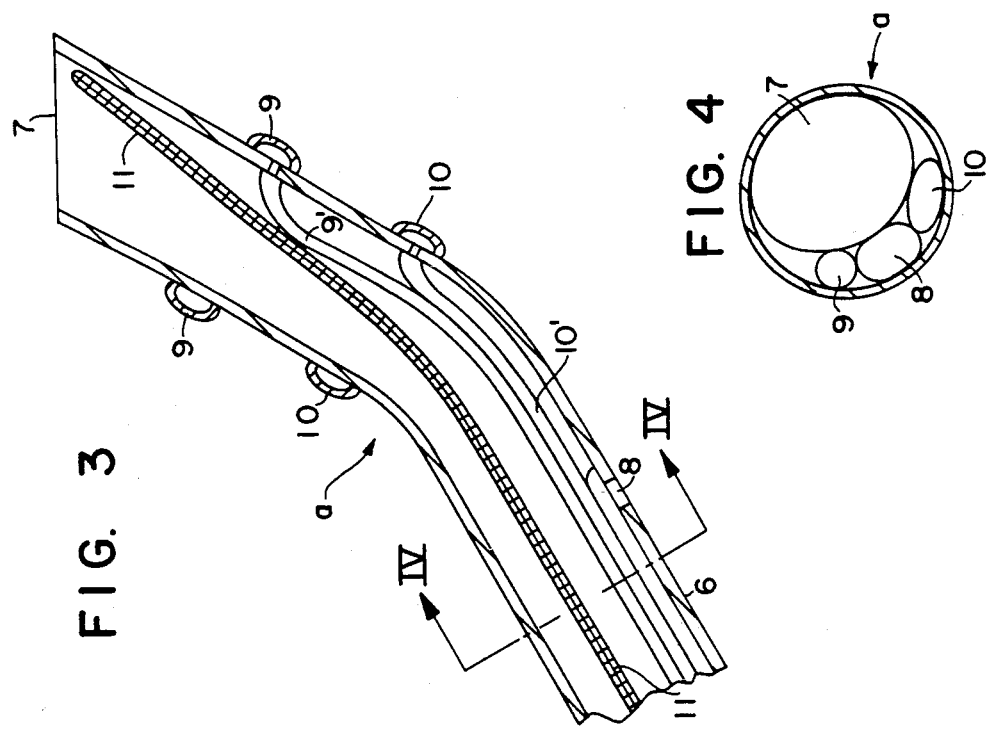
FIG. 3
FIG. 4

ARTERIAL PERFUSION CANNULA FOR EXTRACORPOREAL CIRCULATION AND OTHER USES

This is a continuation of application Ser. No. 737,358 filed Jul. 29, 1991.

BACKGROUND OF THE INVENTION

The instant invention relates to medical devices, and more particularly relates to a cannula for arterial perfusion, for extracorporeal circulation and other uses.

More particularly, the object of the invention is to provide a means capable of effecting extracorporeal blood circulating loop and depuration, without affecting the vessels from which said loop is connected.

Generally, it may be said that heart surgery requires quietness and vacuum of this organ. To this end the heart is connected to an extracorporeal circulating system which drains non oxygenated blood towards a device functioning as heart and lung, restoring oxygenated blood through an arterial perfusion cannula inserted into the aorta or the femoral.

In order to attain a heart free of blood, it is necessary to interrupt blood flow through coronary arteries, which is attained by clamping the ascending aorta applying pliers or clamps which strangulate the vessel thus occluding its longitudinal passage.

For a long time it was considered that, due to the natural elasticity of the arterial walls, the use of such clamps did not cause any problem.

However, recent studies, still under development, have demonstrated that the use of such clamps causes traumatic effects, as well as alterations of the aortic wall and wall thrombi running the risk of brain embolism.

Thus, the object of the invention is to provide an arterial perfusion cannula, i.e. of the re-infusion end of oxygenated blood which, in turn, through the provision of inflatable balloons, allows the function of inner clamp (non traumatic) and coronary perfusion through its proximal opening, infusion of cardioplegic solution or use of the same opening for venting the left heart cavities.

SUMMARY OF THE INVENTION

The arterial perfusion cannula of the invention, for extracorporeal circulation and other uses is of the type used for being inserted into the ascending aorta or into the femorals on one part, and on the other connectable to a cardiopulmonary machine, and comprises a multichannel catheter including at least three pathways, two of which correspond to the inlet of blood flow, provided with openings which, being interconnectable to the aortic vessel, are located at both regions of the end of the cannula, and a third pathway channelizing a fluid feeding at least one inflatable balloon, between said interconnecting openings, as an arterial occlusive element adjustable against the internal vessel walls.

BRIEF DESCRIPTION OF THE DRAWINGS

FIG. 3 is an enlarged longitudinal section, in detail, of the catheter or cannula, showing the balloons, with the inflation channels, as well as circulation pathways for blood inlet from the cardiopulmonary machine; the forming semi-rigid mandrel being also shown schematically in said catheter.

FIG. 4 is a cross-section of the catheter, as per line IV—IV of FIG. 3 showing the way in which it may be applied through the femoral, with one or two inflatable balloons and obviously having a greater length than that used by the ascending aorta pathway.

FIG. 5 is a longitudinal schematic section similar to FIG. 2 showing a further embodiment of the present invention for insertion into a femoral artery.

In different figures, the same reference numerals designate the same or equivalent parts; the assembly of various elements being designated with letters.

DETAILED DESCRIPTION OF THE INVENTION

Figure 2:
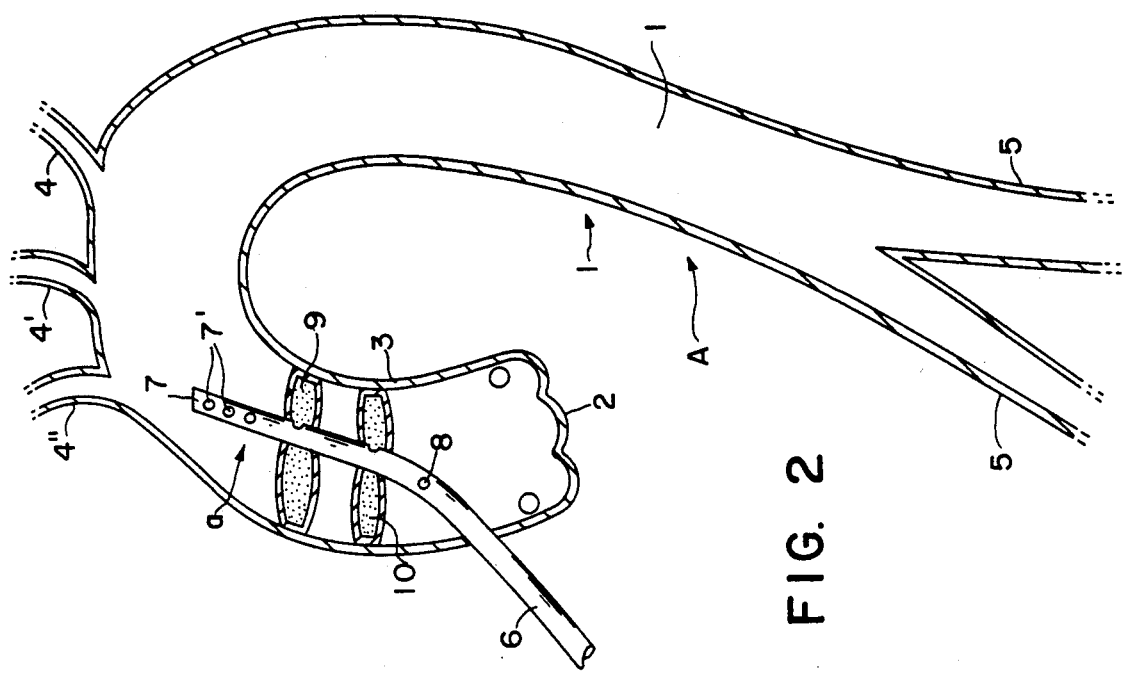
FIG. 2 is another longitudinal schematic section of the same aortic vessel, showing the cannula placed at said ascending aorta, but in an alternative embodiment of the cannula which in this case has two inflatable balloons.

Generally, the cannula of the invention comprises a multi-channel flexible catheter or cannula (a) which is made semi-rigid by means of an elongated mandrel (11), which may be introduced into aortic vessel (A) and withdrawn from its pathways or channels and including catheter end outlet opening (7). Catheter (a) is provided with catheter tubular body end region (6).

More particularly, and as may be seen in the drawings, the catheter or cannula (a) may have three or four channels, see FIGS. 3 and 4. One channel or first pathway is provided at catheter tubular body end region (6) and mates with end opening (7) and/or side openings (7'). A second channel or second pathway has an opening (8) located at an intermediate or side region of body end region (6) spaced from the region at which the end openings (7) and side openings (7') are located A third channel or third pathway (9'), which may include fourth pathway or branch (10') constitutes means for channelizing a fluid for inflating one or two elastic balloons (9) and (10), respectively, each of which has an annular shape, and is fixed by the catheter tubular body end region (6) at a region of body (6) intermediate the region into which openings (8) and (7, 7') already mentioned are located (FIGS. 1 and 2).

Consequently, the end openings (7) and (7') of catheter (a) form a first pathway thereof, the opening (8) forms a second pathway and, between openings (7, 7') on the one hand and opening (8) on the other hand. Third and fourth channels or pathways (9', 10') connect to first and second elastic balloons, respectively (9, 10). The catheter is connected to the power line of a cardiopulmonary machine or equipment and extracorporeal circulation is obtained in order to maintain oxygenation of blood feeding the circulatory system of a patient, when his heart muscle is temporarily stopped due to surgical reasons.

Figure 1:
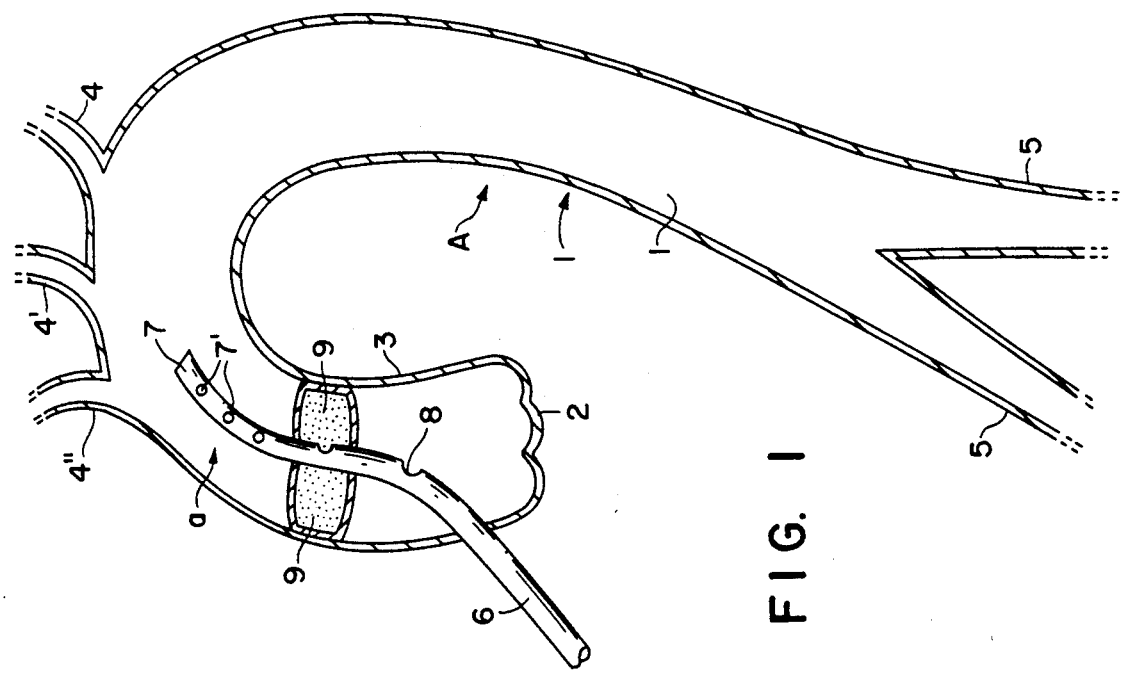
FIG. 1 is a longitudinal schematic section of the aortic vessel, showing the location of the cannula through the ascending aorta, said cannula being provided with a single inflated balloon occluding said vessel region by means of internal adjustment against the inner walls thereof, thus separating two regions in which the inlet openings of the blood flow are located to produce extracorporeal circulation.

The balloon or balloons (9) and (10) act as temporary occlusive elements of the arterial vessel (A) in the ascending aorta (3), and between the lower portion of the aortic valve (2) and its coronary ostium, with respect to the region of the aortic zone in which the left subclavian (4), left carotid (4') and the brachy-cephalic trunk (4") are located, see FIGS. 1, 2 and 5.

Catheter (a) may be introduced through the ascending aorta (3), with only a first or one balloon (9) or a first and second or two balloons (9', 10), as shown in FIGS. 1 and 2, or through femoral pathway (5) as shown in FIG. 5, with one balloon (9) not shown, and also with two occlusive balloons (9, 10) as is clearly seen in FIG. 5. The catheter (a), in the case of the femoral pathway (5), is of a length greater than that to be used for the ascending aorta (3) as shown in FIGS. 1-2.

In this way, when catheter (a) is introduced in any form, with balloons (9) and (10) deflated, and once the catheter is positioned, the only thing to do is to inflate said balloons (9) and (10) through channels (9') and (10') feeding them with the corresponding fluid.

Balloons (9) and (10), made of an elastomer, expand until they tightly bear against the interior of the walls (3) without any injury thereof, but defining a perfect closure isolating the zones of proximal pathways openings designated with (8) for coronary perfusion, infusion of cardioplegic solution or venting of the left heart cavities; while the distal pathway (7—7') is for perfusion in the whole organism (FIGS. 1 and 2).

On the other hand, the third and fourth pathways (9', 10') are for channelizing the fluid for inflating balloons (9) and (10).

In the femoral application (5) of FIG. 5, the location of said cannula pathways is reversed, as may be seen in said figure, so that balloon (10) in FIG. 5 is adjacent to openings (7, 7').

Once perfusion is carried out, the artery (A) is returned to its normal function by deflation of balloons (9, 10) and removal of the cannula (a).

It is obvious that modifications related to construction and shape may be introduced by those skilled in the art without departing from the spirit and scope of the invention, as clearly defined by the appended claims.

We claim:

1. Arterial perfusion cannula, for effecting extracorporeal circulation, wherein one part is inserted into the aortic vessel, and the other part is connected to a cardiopulmonary machine, comprising: a single multi-channel catheter having a tubular body end region and including at least separate and independent first, second and third pathways each of which having corresponding at least one first, second and third openings in said tubular body end region; wherein the first and second pathways define separate non-communicating passages within said catheter; the third pathway comprising a further independent passage in said catheter channelizing a fluid with the corresponding third opening of said third pathway feeding at least one inflatable balloon which is located between the first and second openings, as an arterial occlusive element operative to be adjustable against the internal vessel walls; with the sole openings in the tubular body end region being the first, second and third openings; wherein the first pathway has its sole opening to the tubular body end region in the at least one first opening downstream of said balloon, and the second pathway has its sole opening to the tubular body end region in the at least one second opening upstream of said balloon; and wherein the first pathway and at least one corresponding first opening are of a size suitable for infusion of oxygenated blood from a cardiopulmonary machine for the whole organism in sufficient amounts to maintain circulation.

2. Arterial perfusion cannula, as claimed in claim 1, wherein, in its end region the catheter has fixed thereon pair of spaced apart inflatable balloons, provided between the first and second openings, said inflatable balloons constituting arterial occlusive elements, operative to be adjustable against the inner wall of the aortic vessel.

3. Arterial perfusion cannula, as claimed in claim 1, wherein the inlet pathways of the blood flow through the catheter end at the first and second openings, said first and second openings being positioned at two regions, proximal and distal, respectively, separated by at least one inflatable balloon.

4. Arterial perfusion cannula, as claimed in claim 3, wherein said first opening corresponds to the end of the catheter and comprises an opening at the tip of said catheter and other first side openings adjacent the opening at the tip of the catheter, while the second openings, spaced apart form said first openings, have in turn at least one opening.

5. Arterial perfusion cannula, as claimed in claim 1, wherein the inflatable balloons are of flattened toroidal section, and are fixed against the outer walls of the catheter.

* * * * *